(12) United States Patent
Hirsch et al.

(10) Patent No.: US 6,213,987 B1
(45) Date of Patent: Apr. 10, 2001

(54) SHROUD FOR A USED HYPODERMIC SYRINGE NEEDLE

(76) Inventors: Michael N. Hirsch, 4400 SW. Pomona St., Portland, OR (US) 97219; Jack P. Rosoff, 3332 SE. 28th Ave., Portland, OR (US) 97202; Ali Salem, 1561 NE. Laurelwood Cir., Canby, OR (US) 97013

( * ) Notice: Subject to any disclaimer, the term of this patent is extended or adjusted under 35 U.S.C. 154(b) by 0 days.

(21) Appl. No.: 09/364,996

(22) Filed: Aug. 2, 1999

(51) Int. Cl.⁷ .................................................... A61M 5/00
(52) U.S. Cl. ............................................. 604/263; 604/198
(58) Field of Search .................................. 604/192, 194, 604/263, 110; 128/919

(56) References Cited

U.S. PATENT DOCUMENTS

| | | | |
|---|---|---|---|
| 4,985,021 | 1/1991 | Straw et al. | 604/198 |
| 5,000,740 | 3/1991 | Ducharme et al. | 604/162 |
| 5,019,051 | 5/1991 | Hake | 604/198 |
| 5,026,356 * | 6/1991 | Smith . | |
| 5,053,018 * | 10/1991 | Talonn et al. . | |
| 5,215,534 | 6/1993 | De Harde et al. | 604/198 |
| 5,215,535 * | 6/1993 | Getting et al. . | |
| 5,304,149 * | 4/1994 | Morigi . | |
| 5,385,555 * | 1/1995 | Hausser . | |
| 5,411,492 | 5/1995 | Sturman et al. | 604/263 |
| 5,595,566 * | 1/1997 | Vallelunga et al. . | |
| 5,674,203 * | 10/1997 | Lewandowski . | |
| 5,928,205 * | 7/1999 | Marshall . | |

\* cited by examiner

*Primary Examiner*—Mark Bockelman
(74) *Attorney, Agent, or Firm*—James D. Givnan, Jr.

(57) ABSTRACT

A guide of the device is engageable with a hypodermic syringe barrel for secure placement thereon. A slide carried by the guide includes a shroud extensible from a stowed position adjacent the barrel forward over the end of a used syringe needle. The guide and an elongate slide therein embody locking means retaning the slide in an extended position after syringe use. A rib on the slide is provided at one end with a finger contactible surface for convenient slide positioning. The guide includes inwardly turned flanges to further support the slide against lateral displacement.

5 Claims, 1 Drawing Sheet

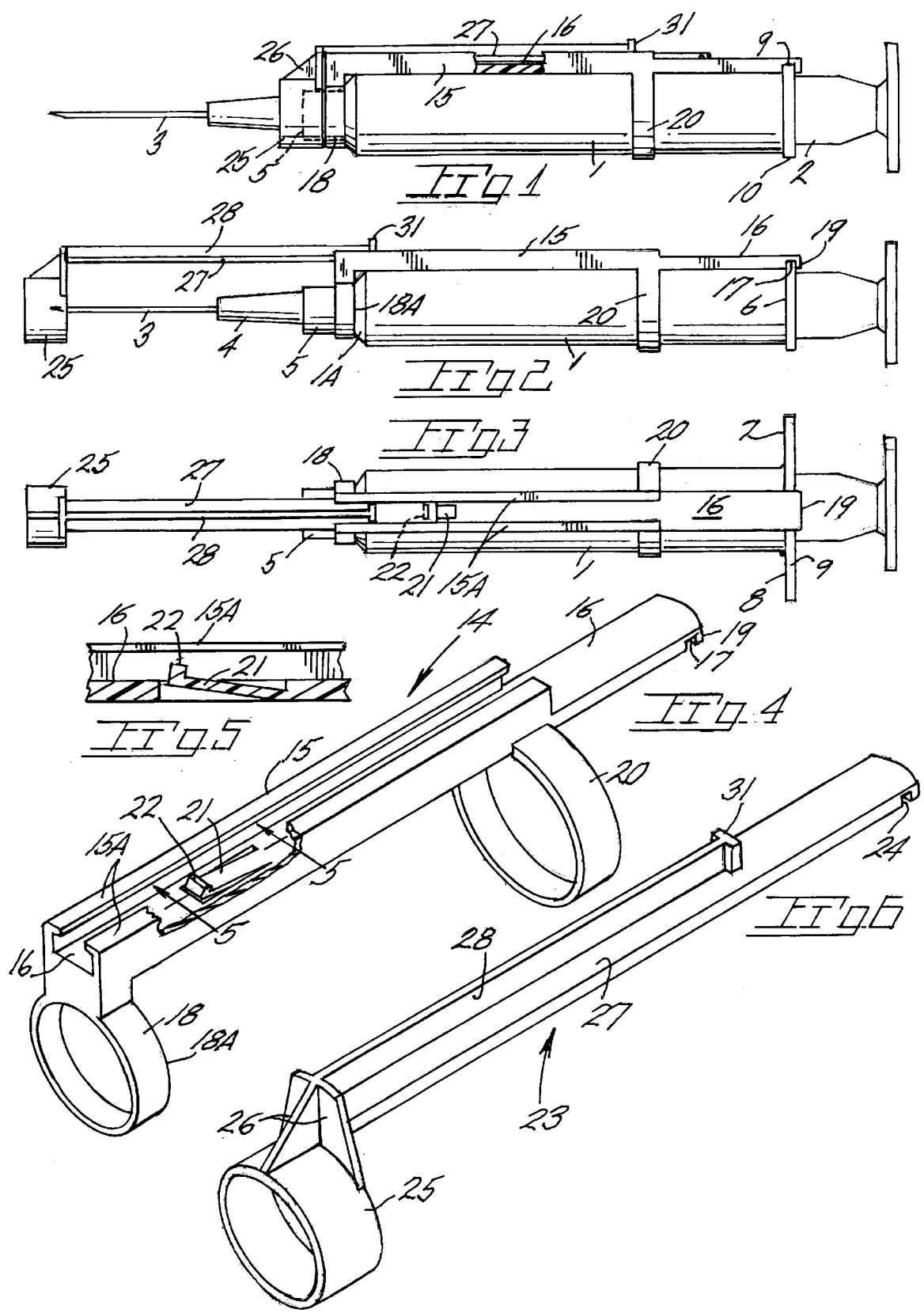

SHROUD FOR A USED HYPODERMIC SYRINGE NEEDLE

BACKGROUND OF THE INVENTION

The present invention concerns the provision of a shroud or guard for disposition about the point of a used hypodermic syringe needle to prevent contact with the needle by medical personnel.

A risk exits to medical personnel of coming into accidental contact with a used hypodermic syringe needle and transmission of an infection from a previously treated individual such as hepatitis and the AIDS virus. While great care is normally exercised by medical personnel to avoid such contact with a used hypodermic needle, such contact does occur. Several solutions to the problem, termed needle stick, have been disclosed in various U.S. patents.

U.S. Pat. No. 5,411,492 shows a hypodermic syringe provided with a needle and hub assembly for attachment to the coupling socket integral with the syringe barrel. The needle hub supports a rail or guide which in turn carries an arm positionable lengthwise of the needle to locate a cap about the poined end of the needle. A cap is normally retracted in place about the needle and hub and repositioned over the needle end subsequent to syringe use. A problem encountered by such an arrangement is that a needle and hub assembly cannot be readily interchanged with another needle and hub assembly as such a change incurs the replacement of the protective device. Further, the manufacturing cost of the a needle and hub assembly with rail structure attached would appear to increase the cost of same. Some risk additionally is encountered upon inadvertent application of a fingertip to the cap of the device which in some instances could displace the cap axially to permit exposure of the needle end therethrough.

U.S. Pat. No. 5,000,740 is of interest in that a needle housing is slidably disposed on a flash chamber and extensible therefrom to locate a needle guard tip about the used needle of the catheter device.

U.S. Pat. No. 4,985,021 discloses a slidably mounted tubular housing on a syringe barrel with a helical spring operable to extend the housing about the end of a needle of the syringe with provision made for preventing retraction of the housing.

U.S. Pat. No. 5,215,534 discloses a needle guard which is positionable by a spring along the length of the needle to its end. A shaft carries a shielding cap with retraction of the cap prevented after extension over the needle end.

U.S. Pat. No. 5,019,051 discloses an assembled protective enclosure for a used needle which encloses the syringe barrel to hinder viewing barrel markings and after use, positioned along the barrel to overlie the needle and needle hub.

SUMMARY OF THE PRESENT INVENTION

The present invention is embodied within a guide with attachment means for placement along the syringe barrel to receive a slide, the distal end of which carries a shroud which isolates the needle end from contact. The guide and slide may be locked to prevent slide retraction after placement about the needle end. The guide insertably receives the syringe barrel and additionally includes a tang for engagement with a syringe flange for retention against displacement relative the barrel. A shroud is stowed about the coupling collar of the syringe and permits interchanging of needles on the syringe when desired. The locking arrangement prevents shroud displacement subsequent to positioning about the needle with locking means concealed from convenient access to prevent accidental shroud retraction. The guide engages the barrel in a manner securing the guide against axial and rotational displacement. An elongate slide in the guide is readily positionable by fingertip pressure to advance the shroud.

Important objectives include the provision of a device for enclosing the end of a used hypodermic syringe needle with the device readily attachable to a syringe and of a low manufacturing cost; the provision of a device for isolating the end of a used hypodermic needle which device does not hinder substitution of a needle assembly as the needle and hub assembly is free of any encumbrance; the provision of a device having a slide lockable in an extended position with the slide being of a cross sectional shape including vertical and horizontal cross section members preventing needle end exposure upon inadvertent contact with the needle shroud; the provision of a device providing for the enclosing of the end of a used hypodermic syringe needle which permits lengthwise positioning of a guide of the device along a hypodermic syringe barrel to virtually avoid obscuring indicia thereon and which is fixed against displacement along and about the barrel; the provision of a needle guard positioned by a finger of the hand holding the syringe.

BRIEF DESCRIPTION OF THE DRAWINGS

In the accompanying drawings:

FIG. 1 is a side elevational view of a hypodermic syringe having the present device for enclosing a used needle end thereon;

FIG. 2 is a view similar to FIG. 1 but with the device operatively disposed with a shroud component enclosing the needle end;

FIG. 3 is a plan view of FIG. 2;

FIG. 4 is a perspective view with fragments broken away of the guide of the present device;

FIG. 5 is a vertical section taken along line 5—5 of FIG. 4, and

FIG. 6 is a perspective view of the slide component of the present device.

DETAILED DESCRIPTION OF THE PREFERRED EMBODIMENTS

With continuing attention to the drawings wherein applied reference numerals indicate parts similarly hereinafter identified, the reference numeral 1 indicates the tubular cylindrical barrel of a hypodermic syringe having a plunger 2 having an unseen end for loading as well as for syringe discharge via a needle 3. The needle 3 is typically part of a needle assembly including a needle hub 4 shown in inserted engagement with a coupling collar 5 integral with syringe barrel 1. Typically needle hub 4 is provided with a lock for engagement with a corresponding shaped internal wall of coupling collar 5. A flange 6 is integral with the rearward end of the syringe and provides fingertip receiving areas 7 and 8 during inward actuation of plunger 2. Typically flanges 7 terminate in rounded ends with intermediate parallel straight edges at 9 and 10.

With attention to the present device for shielding the end of a hypodermic syringe needle, the device includes a guide indicated generally at 14 including rails at 15 extending substantially the length of a guide base 16 which lies lengthwise along barrel 1 and recessed at 17 to receive the upper edge 9 of syringe flange 6. Attachment means includes a first arcuate surface for engageably attaching the device to the coupling collar and a second arcuate surface for engageably attaching the device to the cylindrical portion of the barrel wherein the first and second surfaces are spaced apart so as to permit manual grasping of the barrel to be positioned therebetween. One form of the attachment means includes a ring 18 at the forward end of base 16 of a size to fit in a precise manner about coupling collar 5 with a ring edge 18A seating against barrel end 1A and a second ring 20. Accordingly, guide 14 is prevented from rearward displacement along barrel 1 and prevented from moving in the opposite direction by engagement of recess 17, at the rearward end of a base being in seated engagement with edge 9 of barrel flange 6. The second ring at 20 is adapted for positioning along cylindrical barrel 1 and is sized to accommodate the barrel in a manner preventing lateral movement therebetween. A tang 19 abuts barrel flange 6.

Locking means are best viewed in FIG. 4 and include an arm 21 provided with a detent 22 at its free end which is inherently biased above the adjacent to surface of base 16. The arm is flexible to the extent to admit rearward insertion of a slide indicated generally at 23 and having a recess 24 at its rearward end for locking engagement with detent 22.

Slide 23 carries a shroud 25 which may be of circular configuration and carried at the slide end by a connector 26 integral with a slide main member 27 and with a rib 28 thereon extending therealong to inhibit flexure of the slide. In a retracted or inoperative state shroud 25 may be partially disposed about coupling sleeve 5 rearward of the needle hub 4 to prevent hindering of needle removal and substitution. A finger actuated appendage 31 facilitates imparting lengthwise movement to slide 23 until engagement of slide recess 24 with lock detent 22 which occurs simultaneously with the shroud 25 being circumposed about the needle end.

In use, the shroud can be advanced to the extended or operable position after an injection by the user exerting thumb or finger pressure on slide recess 24. Such positioning is preferably done with a finger or thumb of the hand holding the syringe which avoids bringing the remaining hand into the proximity of the used needle.

While the attachment means are shown to include rings 18 and 20 in the preferred form of the device, in some applications of the present device it may be desirable to alternatively provide legs with arcuate surfaces thereon for engagement with, respectively, the coupling collar and the barrel of the syringe.

While we have shown but one embodiment of the invention, it will be apparent to those skilled in the art that the invention may be embodied still otherwise without departing from the spirit and scope of the invention.

Having thus described the invention, what is desired to be secured by a Letters Patent is:

We claim:

1. A device for shielding the distal end of a used needle of a hypodermic syringe having a barrel with a cylindrical portion and a coupling collar for attaching a needle thereto, said device including, a guide including attachment means having a first arcuate surface for engageably attaching the device to the coupling collar and a second arcuate surface for engageably attaching the device to the cylindrical portion of the barrel, wherein the first and second surfaces are spaced apart so as to permit manual grasping of the barrel to be positioned therebetween, an elongate slide carried by said guide and having a shroud at one end, said slide having a retracted inoperative position in juxtapositon with the syringe barrel with the shroud in place about the coupling collar, said slide having an operable extended position locating said shroud about the distal end of a used needle, and locking means on said guide and said slide operable upon extension of the slide for locking the slide extended in place relative the guide.

2. The device claimed in claim 1 wherein said attachment means arcuate surfaces are ring members.

3. The device claimed in claim 1 wherein said attachment means additionally includes a tang for engagement with the syringe barrel.

4. The device claimed in claim 1 wherein said slide includes a lengthwise extending rib imparting rigidity to the slide and the rib thereon, a connector attaching said slide to the shroud.

5. The device claimed in claim 1 wherein said locking means includes an arm carried detent biased toward a recess positionable proximate said detent concurrent with shroud advancement into the operable extended position.

\* \* \* \* \*